(12) United States Patent
Gefter et al.

(10) Patent No.: US 6,180,608 B1
(45) Date of Patent: *Jan. 30, 2001

(54) PHARMACEUTICAL FORMULATIONS FOR SUSTAINED DRUG DELIVERY

(75) Inventors: Malcolm L. Gefter, Lincoln; Nicholas Barker, Southborough; Gary Musso, Hopkinton; Christopher J. Molineaux, Brookline, all of MA (US)

(73) Assignee: Praecis Pharmaceuticals, Inc., Cambridge, MA (US)

( * ) Notice: Under 35 U.S.C. 154(b), the term of this patent shall be extended for 0 days.

This patent is subject to a terminal disclaimer.

(21) Appl. No.: 08/988,851

(22) Filed: Dec. 11, 1997

Related U.S. Application Data

(63) Continuation-in-part of application No. 08/762,747, filed on Dec. 11, 1996, now Pat. No. 5,968,895.

(51) Int. Cl.$^7$ .................................................. A61K 38/00
(52) U.S. Cl. ................................ 514/13; 514/14; 514/15; 514/16; 514/800; 530/313; 530/326; 530/327; 530/328; 530/329; 530/330; 424/468; 424/486; 424/488; 424/499
(58) Field of Search ................................ 514/13, 14, 15, 514/16, 800; 530/313, 326–330; 424/468, 486, 488, 499

(56) References Cited

U.S. PATENT DOCUMENTS

| | | |
|---|---|---|
| 3,963,691 * | 6/1976 | Hoffman et al. ............. 260/112.5 LH |
| 4,010,125 * | 3/1977 | Schally et al. ............. 260/8 |
| 4,016,100 | 4/1977 | Suzuki et al. ............. 252/316 |
| 4,389,393 | 6/1983 | Schor et al. ............. 424/19 |
| 4,526,938 | 7/1985 | Churchill et al. ............. 525/415 |
| 4,610,868 | 9/1986 | Fountain et al. ............. 424/1.1 |
| 4,613,500 | 9/1986 | Suzuki et al. ............. 429/85 |
| 4,639,370 | 1/1987 | Carli ............. 424/80 |
| 4,675,189 | 6/1987 | Kent et al. ............. 424/490 |
| 4,677,191 | 6/1987 | Tanaka et al. ............. 528/361 |
| 4,728,721 | 3/1988 | Yamamoto et al. ............. 528/361 |
| 4,775,535 | 10/1988 | Lowey ............. 424/468 |
| 4,789,547 | 12/1988 | Song et al. ............. 424/449 |
| 4,897,268 * | 1/1990 | Tice et al. ............. 424/422 |
| 4,913,906 | 4/1990 | Friedman et al. ............. 424/499 |
| 4,980,150 | 12/1990 | Keith ............. 424/490 |
| 5,015,479 | 5/1991 | Mulligan et al. ............. 424/457 |
| 5,028,430 | 7/1991 | Sanders et al. ............. 424/423 |

(List continued on next page.)

FOREIGN PATENT DOCUMENTS

| | | |
|---|---|---|
| 328090 | 8/1989 | (EP) . |
| 467389 | 1/1992 | (EP) . |
| 601799 | 6/1994 | (EP) . |
| 2455459 | 1/1981 | (FR) . |
| 63310827 | 12/1988 | (JP) . |
| WO 88/05661 | 8/1988 | (WO) . |
| WO 92/11844 | 7/1992 | (WO) . |
| WO 92/20349 | 11/1992 | (WO) . |
| WO 94/08566 | 4/1994 | (WO) . |
| WO 94/15587 | 7/1994 | (WO) . |
| WO 96/39160 | 12/1996 | (WO) . |
| WO 96/40757 | 12/1996 | (WO) . |
| WO 97/22357 | 6/1997 | (WO) . |

OTHER PUBLICATIONS

Hussain, M. A. et al., "Injectable suspensions for prolonged release nalbuphine," *Drug Devel. And industrial pharmacy,* 17(1):67–76 (1991).

Langer, R.(1982), "Controlled Release of Macromolecules," *Chemtech* 12(2):98–105.

Paavola, A. et al., "Controlled release of lidocaine from injectable gels and efficacy in rat sciatic nerve block," *Pharm. Res.* 12(12):1997–2002 (1995).

Palyi, I. Et al., "Effect of gonadotropin–releasing hormone analogs and their conjugates on gonadotropin–releasing hormone receptor–positive human cancer cell lines," *Cancer Detection and Prevention,* 20(2):146–152, (1996).

Vincze, B. et al., "Antitumour effect of a gonadotropin–releasing hormone antagonist (MI–1544) and its conjugate on human breast cancer cells and their xenografts," *J. Cancer Res. Clin. Oncol.,* 120(10):578–584.

AN 1991: 49580 HCAPLUS, EP 36800, abstract, 1990.*
AN 1993: 198209 HCAPLUS, DE 4223282, abstract.*
AN 1989: 141530 HCAPLUS, WO 8805661, abstract, 1988.*
AN 1976: 5401 HCAPLUS, DE 2509783, abstract, 1975.*
ON 99324328 Biosis, Mezo et al., *Bioconjugate Chemistry,* 7(6), 642–650, (abstract), 1996.*
ON 108: 192636 CAPLUS, Kaetsu et al., *J. Controlled Release,* 6, 249–63 (abstract), 1987.*

* cited by examiner

*Primary Examiner*—Marianne M. Cintins
*Assistant Examiner*—C. Delacroix-Muirheid
(74) *Attorney, Agent, or Firm*—Lahive & Cockfield, LLP; Giulio A. DeConti, Jr.; Maria C. Laccotripe

(57) ABSTRACT

Sustained delivery formulations comprising a water-insoluble complex of a peptidic compound (e.g., a peptide, polypeptide, protein, peptidomimetic or the like) and a carrier macromolecule are disclosed. The formulations of the invention allow for loading of high concentrations of peptidic compound in a small volume and for delivery of a pharmaceutically active peptidic compound for prolonged periods, e.g., one month, after administration of the complex. The complexes of the invention can be milled or crushed to a fine powder. In powdered form, the complexes form stable aqueous suspensions and dispersions, suitable for injection. In a preferred embodiment, the peptidic compound of the complex is an LHRH analogue, preferably an LHRH antagonist, and the carrier macromolecule is an anionic polymer, preferably carboxymethylcellulose. Methods of making the complexes of the invention, and methods of using LHRH-analogue-containing complexes to treat conditions treatable with an LHRH analogue, are also disclosed.

50 Claims, 5 Drawing Sheets

U.S. PATENT DOCUMENTS

| | | | |
|---|---|---|---|
| 5,049,395 | 9/1991 | Chang | 424/494 |
| 5,128,142 | 7/1992 | Mulligan et al. | 424/457 |
| 5,180,522 | 1/1993 | Kawashima et al. | 252/311 |
| 5,192,741 | 3/1993 | Orsolini et al. | 514/4 |
| 5,314,915 | 5/1994 | Rencher | 514/535 |
| 5,326,571 | 7/1994 | Wright et al. | 424/473 |
| 5,366,734 | 11/1994 | Hutchinson | 424/426 |
| 5,439,688 | 8/1995 | Orsolini et al. | 424/489 |
| 5,462,749 | 10/1995 | Rencher | 424/484 |
| 5,480,656 | 1/1996 | Okada et al. | 424/493 |
| 5,487,898 | 1/1996 | Lu et al. | 424/435 |
| 5,520,927 | 5/1996 | Kim et al. | 424/450 |
| 5,540,937 | 7/1996 | Billot et al. | 424/489 |
| 5,545,409 | 8/1996 | Laurencin et al. | 424/426 |
| 5,595,760 | 1/1997 | Cherif-Cheikh | 424/464 |
| 5,629,009 | 5/1997 | Laurencin et al. | 424/426 |
| 5,637,309 * | 6/1997 | Tajima et al. | 424/423 |
| 5,656,297 | 8/1997 | Bernstein et al. | 424/484 |
| 5,688,530 | 11/1997 | Bodmer et al. | 424/501 |
| 5,700,486 | 12/1997 | Canal et al. | 424/501 |
| 5,711,968 | 1/1998 | Tracy et al. | 424/487 |

PHARMACEUTICAL FORMULATIONS FOR SUSTAINED DRUG DELIVERY

RELATED APPLICATION

This application is a continuation-in-part of U.S. patent application Ser. No. 08/762,747, filed Dec. 11, 1996, now U.S. Pat. No. 5,968,895, the entire contents of which are hereby incorporated by reference.

BACKGROUND OF THE INVENTION

A variety of diseases and clinical disorders are treated by the administration of a pharmaceutically active peptide. One such example is prostate cancer, which is a sex hormone dependent cancer and which can be treated by administration of a luteinizing hormone releasing hormone (LHRH) analogue that disturbs the production of luteinizing hormone (LH), which regulates the synthesis of male hormones. In particular, to decrease LH production, peptidic analogues of LHRH that act as superagonists of the luteinizing hormone releasing hormone receptor, such as leuprolide and goserelin, have been used.

In many instances, the therapeutic effectiveness of a pharmaceutically active peptide depends upon its continued presence in vivo over prolonged time periods. To achieve continuous delivery of the peptide in vivo, a sustained release or sustained delivery formulation is desirable, to avoid the need for repeated administrations. One approach for sustained drug delivery is by microencapsulation, in which the active ingredient is enclosed within a polymeric membrane to produce microparticles. For example, LHRH superagonists, such as leuprolide and goserelin, typically are encapsulated within a microparticle comprising a poly-lactide/poly-glycolide copolymer to prepare formulations suitable for depot injection that provide sustained delivery of the superagonist over several weeks to months (see e.g., U.S. Pat. Nos. 4,675,189; 4,677,191; 5,480,656 and 4,728,721).

Additional sustained delivery formulations for administering pharmaceutically active peptides in vivo continuously for prolonged time periods are needed.

SUMMARY OF THE INVENTION

The present invention provides pharmaceutical compositions comprising a stable water-insoluble complex composed of a peptidic compound (e.g., a peptide, polypeptide, protein, peptidomimetic and the like), preferably a pharmaceutically active peptidic compound, and a carrier macromolecule that allow for sustained delivery of the peptide compound in vivo upon administration of the complex. Accordingly, the complex of the invention can permit continuous delivery of a pharmaceutically active peptidic compound to a subject for prolonged periods of time, e.g., one month. Moreover, the association of the peptidic compound and the carrier macromolecule in a tight, stable complex allows for loading of high concentrations of the peptidic compound into the formulation.

The complex of the invention is formed by combining the peptidic compound and the carrier macromolecule under conditions such that a substantially water-insoluble complex is formed, e.g., aqueous solutions of the peptidic compound and carrier macromolecule are mixed until the complex precipitates. The complex may be in the form of a solid (e.g., a paste, granules, a powder or a lyophilizate) or the powdered form of the complex can be pulverized finely enough to form stable liquid suspensions or semi-solid dispersions.

In a preferred embodiment, the peptidic compound of the water-insoluble complex is an LHRH analogue, more preferably an LHRH antagonist, and the carrier macromolecule is an anionic polymer, preferably carboxymethylcellulose. The complex of the invention is suitable for sterilization, such as by gamma irradiation or electron beam irradiation, prior to administration in vivo.

Method for treating a subject for a condition treatable with an LHRH analogue by administering to the subject an LHRH-analogue-containing composition of the invention are also provided. In a preferred embodiment, the treatment methods of the invention are used in the treatment of prostate cancer.

DETAILED DESCRIPTION OF THE INVENTION

Figure 1A:
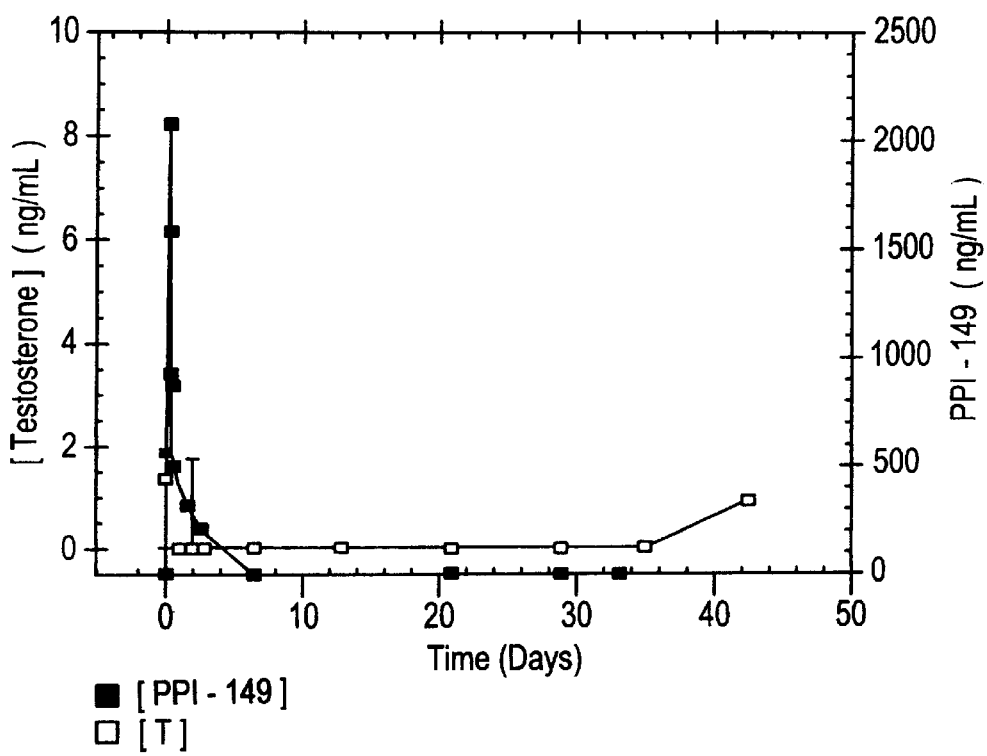
FIG. 1 shows graphs depicting the plasma testosterone levels (in ng/ml; open black boxes) and plasma PPI-149 levels (in ng/ml; closed boxes) in rats (left graph) and dogs (right graph) over time following intramuscular injection of a complex of PPI-149 and carboxymethylcellulose.

This invention pertains to pharmaceutical compositions comprising a stable water-insoluble complex composed of a peptidic compound (e.g., a peptide, polypeptide, protein, peptidomimetic and the like) and a carrier macromolecule, methods of making such compositions and methods of using such compositions. The advantages of the pharmaceutical compositions of the invention include the ability for delivery of a pharmaceutically active peptidic compound, either systemically or locally, for prolonged periods (e.g., several weeks, one month or several months) and the ability to load high concentrations of peptidic compound into the complex.

In order that the invention may be more readily understood, certain terms are first defined.

As used herein, the term "peptidic compound" is intended to refer to compounds composed, at least in part, of amino acid residues linked by amide bonds (i.e., peptide bonds). The term "peptidic compound" is intended to encompass peptides, polypeptide and proteins. Typically, a peptide will be composed of less than about 100 amino acids, more typically less than about 50 amino acid residues and even more typically, less than about 25 amino acid residues. The term "peptidic compound" is further intended to encompass peptide analogues, peptide derivatives and peptidomimetics that mimic the chemical structure of a peptide composed of naturally-occurring amino acids. Examples of peptide analogues include peptides comprising one or more non-natural amino acids. Examples of peptide derivatives include peptides in which an amino acid side chain, the peptide backbone, or the amino- or carboxy-terminus has been derivatized (e.g., peptidic compounds with methylated amide linkages). Examples of peptidomimetics include peptidic compounds in which the peptide backbone is substituted with one or more benzodiazepine molecules (see e.g., James, G. L. et al. (1993) *Science* 260:1937–1942), "inverso" peptides in which all L-amino acids are substituted with the corresponding D-amino acids, "retro-inverso" peptides (see U.S. Pat. No. 4,522,752 by Sisto) in which the sequence of amino acids is reversed ("retro") and all L-amino acids are replaced with D-amino acids )"inverso") and other isosteres, such as peptide back-bone (i.e., amide bond) mimetics, including modifications of the amide nitrogen, the α-carbon, amide carbonyl, complete replacement of the amide bond, extensions, deletions or backbone crosslinks. Several peptide backbone modifications are known, including $\psi[CH_2S]$, $\psi[CH_2NH]$, $\psi[CSNH_2]$, $\psi[NHCO]$, $\psi[COCH_2]$, and $\psi[(E)$ or $(Z)$ CH=CH]. In the nomenclature used above, $\psi$ indicates the absence of an amide bond. The structure that replaces the amide group is specified within the brackets. Other possible modifications include an N-alkyl (or aryl) substitution ($\psi[CONR]$), backbone crosslinking to construct lactams and other cyclic structures, and other derivatives including C-terminal hydroxymethyl derivatives, O-modified derivatives and N-terminally modified derivatives including substituted amides such as alkylamides and hydrazides.

As used herein, the term "pharmaceutically active peptidic compound" is intended to refer to a peptidic compound that exhibits pharmacologic activity, either in its present form or upon processing in vivo (i.e., pharmaceutically active peptidic compounds include peptidic compounds with constitutive pharmacologic activity and peptidic compounds in a "prodrug" form that have to be metabolized or processed in some way in vivo following administration in order to exhibit pharmacologic activity).

As used herein, the terms "multivalent cationic peptidic compound" and "multivalent anionic peptidic compound" are intended to refer to peptidic compounds comprising a multiplicity of positive or negative charges, respectively. A "bivalent cationic" or "bivalent anionic" peptidic compound is intended to refer to a peptidic compound comprising two positive or negative charges, respectively. A "trivalent cationic" or "trivalent anionic" peptidic compound is intended to refer to a peptidic compound comprising three positive or negative charges, respectively.

As used herein, the term "LHRH analogue" is intended to encompass peptidic compounds that mimic the structure of luteinizing hormone releasing hormone. An LHRH analogue may be an LHRH agonist or an LHRH antagonist.

As used herein, an "LHRH agonist" is intended to refer to a compound which stimulates the luteinizing hormone releasing hormone receptor (LHRH-R) such that release of luteinizing hormone is stimulated, or an "LHRH antagonist", which refers to a compound that inhibits LHRH-R such that release of luteinizing hormone is inhibited. Examples of LHRH agonists include leuprolide (trade name: Lupron®; Abbott/TAP), goserelin (trade name: Zoladex®; Zeneca), buserelin (Hoechst), triptorelin (also known as Decapeptyl, D-Trp-6-LHRH and Debiopharm®; Ipsen/Beaufour), nafarelin (trade name" Synarel®; Syntex), lutrelin (Wyeth), cystorelin (Hoechst), gonadorelin (Ayerst) and histrelin (Ortho).

As used herein, the term "LHRH antagonist" is intended to refer to a compound that inhibits the luteinizing hormone releasing hormone receptor such that release of luteinizing hormone is inhibited. Examples of LHRH antagonists include Antide, Cetrorelix, compounds described in U.S. Pat. No. 5,470,947 to Folkers et al.; PCT Publication No. WO 89/01944 by Folkers et al.; U.S. Pat. No. 5,413,990 to Haviv; U.S. Pat. No. 5,300,492 to Haviv; U.S Pat. No. 5,371,070 to Koerber et al.; U.S. Pat. No. 5,296,468 to Hoeger et al.; U.S. Pat. No. 5,171,835 to Janaky et al.; U.S. Pat. No. 5,003,011 to Coy et al.; U.S. Pat. No. 4,431,635 to Coy; U.S. Pat. No. 4,992,421 to De et al.; U.S. Pat. No. 4,851,385 to Roeske; U.S. Pat. No. 4,801,577 to Nestor, Jr. et al.; and U.S. Pat. No. 4,689,396 to Roeske et al. and compounds disclosed in U.S. patent application Ser. No. 08/480,494, entitled "LHRH Antagonist Peptides", and a corresponding PCT application thereof (PCT Application No. PCT/US96/09852), also entitled "LHRH Antagonist Peptides", the entire contents of both of which are expressly incorporated herein by reference. An especially preferred LHRH antagonist comprises the structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH, referred to herein as PPI-149.

As used herein, the term "carrier macromolecule" is intended to refer to a macromolecule that can complex with a peptidic compound to form a water-insoluble complex. Prior to complexing with the peptidic compound, the carrier macromolecule typically is water-soluble. Preferably, the macromolecule has a molecular weight of at least 5 kDa, more preferably 10 kDa. The term "anionic carrier macromolecule" is intended to include negatively charged high molecular weight molecules, such as anionic polymers. The term "cationic carrier macromolecule" is intended to includes positively charged high molecular weight molecules, such as cationic polymers.

As used herein, the term "water-insoluble complex" is intended to refer to a physically and chemically stable complex that forms upon appropriate combining of a peptidic compound and carrier macromolecule according to procedures described herein. This complex typically takes the form of a precipitate that is produced upon combining aqueous preparations of the peptidic compound and carrier macromolecule. Although not intending to be limited by mechanism, the formation of preferred water-insoluble complexes of the invention is thought to involve (i.e., be mediated at least in part by) ionic interactions in situations where the peptidic compound is cationic and the carrier molecule is anionic or vice versa. Additionally or alternatively, the formation of a water-insoluble complex of the invention may involve (i.e., be mediated at least in part by) hydrophobic interactions. Still further, formation of a water-insoluble complex of the invention may involve (i.e., be mediated at least in part by) covalent interactions. Description of the complex as being "water-insoluble" is intended to indicate that the complex does not substantially or readily dissolve in water, as indicated by its precipitation from aqueous solution. However, it should be understood that a "water-insoluble" complex of the invention may exhibit limited solubility (i.e., partial solubility) in water either in vitro or in the aqueous physiological environment in vivo.

As used herein, the term "sustained delivery" is intended to refer to continual delivery of a pharmaceutical agent in vivo over a period of time following administration, preferably at least several days, a week or several weeks. Sustained delivery of the agent can be demonstrated by, for example, the continued therapeutic effect of the agent over time (e.g., for an LHRH analogue, sustained delivery of the analogue can be demonstrated by continued suppression of testosterone synthesis over time). Alternatively, sustained delivery of the agent may be demonstrated by detecting the presence of the agent in vivo over time.

As used herein, the term "subject" is intended to include warm-blooded animals, preferably manunals, more preferably primates and most preferably humans.

As used herein, the term "administering to a subject" is intended to refer to dispensing, delivering or applying a composition (e.g., pharmaceutical formulation) to a subject by any suitable route for delivery of the composition to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

As used herein, the term "a condition treatable with an LHRH analogue" is intended to include diseases, disorders and other conditions in which administration of an LHRH agonist or LHRH antagonist has a desired effect, e.g., a therapeutically beneficial effect. Examples of conditions treatable with an LHRH analogue include hormone-dependent cancers (including prostate cancer, breast cancer, ovarian cancer, uterine cancer and testicular cancer), benign prostatic hypertrophy, precocious puberty, endometriosis, uterine fibroids, infertility (through in vitro fertilization) and fertility (i.e., contraceptive uses).

One aspect of the present invention pertains to a pharmaceutical composition comprising a water-insoluble complex of a pharmaceutically active peptidic compound and a carrier macromolecule. In a preferred embodiment, formation of the water-insoluble complex is mediated at least in part by ionic interactions between the pharmaceutically active peptidic and the carrier macromolecule. In these embodiments, either the pharmaceutically active peptidic compound is cationic and the carrier macromolecule is anionic or the pharmaceutically active peptidic compound is anionic and the carrier macromolecule is cationic. In another embodiment, formation of the water-insoluble complex is mediated at least in part by hydrophobic interactions between the pharmaceutically active peptidic compound and the carrier macromolecule. In a preferred embodiment, the peptidic compound used in the complex is a multivalent cationic peptidic compound, such as a bivalent or trivalent cationic peptidic compound and the carrier macromolecule is an anionic macromolecule.

The pharmaceutical compositions of the invention permit sustained delivery of the peptidic compound to a subject in vivo after administering the composition to the subject, wherein the duration of the sustained delivery can be varied depending upon the concentration of peptidic compound and carrier macromolecule used to form the complex. For example, in one embodiment, a single dose of the water-insoluble complex provides sustained delivery of the peptidic compound to a subject for at least one week after the pharmaceutical composition is administered to the subject. In another embodiment, a single dose of the water-insoluble complex provides sustained delivery of the peptidic compound to a subject for at least two weeks after the pharmaceutical composition is administered to the subject. In yet another one embodiment, a single dose of the water-insoluble complex provides sustained delivery of the peptidic compound to a subject for at least three weeks after the pharmaceutical composition is administered to the subject. In still another embodiment, a single dose of the water-insoluble complex provides sustained delivery of the peptidic compound to a subject for at least four weeks after the pharmaceutical composition is administered to the subject. Formulations that provide sustained delivery for longer or shorter durations are also encompassed by the invention, such as formulations that provide continuous delivery for 1 day, 1–7 days, one month, two months, three months, and the like. Continuous delivery of the peptidic compound for a period of several months can be accomplished, for example, by repeated monthly dosages, each of which provide sustained delivery of the peptidic compound for approximately one month (see e.g., Example 14).

Any size peptidic compound may be suitable for use in the complex as long as the peptidic compound has the ability to form a water-insoluble noncovalent complex with the carrier macromolecule upon combination of the peptidic compound and carrier macromolecule. However, in certain preferred embodiments, the peptidic compound is a peptide that is about 5 to about 20 amino acids in length, about 8 to about 15 amino acids in length or about 8 to about 12 amino acids in length. A variety of pharmaceutically active peptides may be used in the formulations, non-limiting examples of which include LHRH analogues (discussed further below), bradykinin analogues, parathyroid hormone, adenocorticotrophic hormone (ACTH), calcitonin, and vasopressin analogues (e.g, 1-deamino-8-D-arginine vasopressin (DDAVP)).

Although a variety of carrier macromolecules may be suitable for formation of the water-insoluble complexes of the invention, preferred macromolecules are polymers, preferably water-soluble polymers. In a preferred embodiment, the carrier macromolecule is an anionic polymer, such as an anionic polyacohol derivative, or fragment thereof, and salts thereof (e.g., sodium salts). Anionic moieties with which the polyalcohol can be derivatized include, for example, carboxylate, phosphate or sulfate groups. A particularly preferred anionic polymer is an anionic polysaccharide derivative, or fragment thereof, and salts thereof (e.g., sodium salts). The carrier macromolecule may comprise a single molecular species (e.g., a single type of polymer) or two or more different molecular species (e.g., a mixture of two types of polymers). Examples of specific anionic polymers include carboxymethylcellulose, align, alginate, anionic acetate polymers, anionic acrylic polymers, xantham gums, sodium starch glycolate, and fragments, derivatives and pharmaceutically acceptable salts thereof, as well as anionic carageenan derivatives, anionic polygalacturonic acid derivatives, and sulfated and sulfonated polystyrene derivatives. A preferred anionic polymer is carboxymethylcellulose sodium salt. Examples of cationic polymers include poly-L-lysine and other polymers of basic amino acids.

In a particularly preferred embodiment of the invention, the peptidic compound of the water-insoluble complex is an LHRH analogue, for example an LHRH agonist or, more preferably, an LHRH antagonist. Such LHRH analogues typically are 10 amino acids in length. Preferred LHRH antagonists include LHRH antagonists that comprise a peptide compound, wherein a residue of the peptide compound corresponding to the amino acid at position 6 of natural mammalian LHRH comprises a D-asparagine (D-Asn) structure. As used herein, the term "D-asparagine structure" is intended to include D-Asn and analogues, derivatives and mimetic thereof that retain the functional activity of D-Asn. Other preferred LHRH antagonists include LHRH antagonists that comprise a peptidic compound comprising a structure: A-B-C-D-E-F-G-H-I-J
wherein
  A is pyro-Glu, Ac-D-Nal, Ac-D-Qal, Ac-Sar, or Ac-D-Pal
  B is His or 4-Cl-D-Phe
  C is Trp, D-Pal, D-Nal, L-Nal, D-Pal(N-O), or D-Trp
  D is Ser
  E is N-Me-Ala, Tyr, N-Me-Tyr, Ser, Lys(iPr), 4-Cl-Phe, His, Asn, Met, Ala, Arg or Ile;
  F is

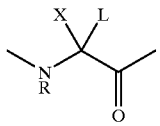

wherein
    R and X are, independently, H or alkyl; and
    L comprises a small polar moiety;
  G is Leu or Trp;
  H is Lys(iPr), Gln, Met, or Arg
  I is Pro; and
  J is Gly-NH$_2$ or D-Ala-NH$_2$;
or a pharmaceutically acceptable salt thereof.

The term "small polar moiety" refers to a moiety which has small steric bulk and is relatively polar. Polarity is measured as hydrophilicity by the P scale. The partition coefficient, P, between 1-octanol and water has been used as a reference for measuring the hydrophilicity of a compound. Hydrophilicity can be expressed as log P, the logarithm of the partition coefficient (Hansch et al., *Nature* 194:178 (1962); Fujita et al., *J. Am. Chem. Soc.* 86:5175 (1964)). Standard tables of hydrophilicity for many molecules, and lipophilicity (hydrophobicity) substituent constants (denoted π) for many functional groups, have been compiled (see, e.g., Hansch and Leo, "Substituent Constants for Correlation Analysis in Chemistry and Biology," Wiley, New York, N.Y., (1979)). The hydrophilicity of a vast range of candidate hydrophilicity moieties can be quite accurately predicted with the aid of these tables. For example, the measured log P (octanol/water) of naphthalene is 3.45. The substituent constant p for —OH is −0.67. Therefore, the predicted log P for β-naphthol is 3.45 +(−0.67)=2.78. This value is in good agreement with the measured log P for β-naphthol, which is 2.84. As used herein, the term "small polar moiety" refers to moieties that have a log P between −1 and +2 and a steric bulk that is less than the steric bulk of Trp.

In certain embodiments, L comprises a small polar moiety with the proviso that F is not D-Cit, D-Hci or a lower alkyl derivative of D-Cit or D-Hci. Preferably, F is selected from the group consisting of D-Asn, D-Gln and D-Thr. More preferably, F is D-Asn. Preferably, E is tyrosine (Tyr) or N-methyl-tyrosine (N-Me-Tyr). In a particularly preferred embodiment, the LHRH antagonist has the following structure: Ac-D-Nal[1], 4-Cl-D-Phe[2], D-Pal[3], N-Me-Tyr[5], D-Asn[6], Lys(iPr)[8], D-Ala[10]-LHRH (referred to herein as PPI-149). A particularly preferred complex of the invention comprises PPI-149 and carboxymethylcellulose.

In addition to the water-insoluble complex, the pharmaceutical formulations of the invention can comprise additional pharmaceutically acceptable carriers and/or excipients. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Excipients include pharmaceutically acceptable stabilizers and disintegrants.

In addition to pharmaceutical formulations of LHRH analogues complexed with a carrier macromolecule, the invention further encompasses packaged formulations containing such complexes and syringes containing such complexes. For example, the invention provides a packaged formulation for treating a subject for a condition treatable with an LHRH analogue, comprising a water-insoluble complex of an LHRH analogue (preferably PPI-149) and a carrier macromolecule (preferably carboxymethylcellulose), packaged with instructions for using the water-insoluble complex for treating a subject for a condition treatable with an LHRH analogue. In another embodiment, the invention provides a syringe having a lumen, wherein a water-insoluble complex of an LHRH analogue (preferably PPI-149) and a carrier macromolecule (preferably, carboxymethyl-cellulose) is included in the lumen.

The complex of the invention is prepared by combining the peptidic compound and the carrier macromolecule under conditions such that a water-insoluble complex of the peptidic compound and the carrier macromolecule forms. Accordingly, another aspect of the invention pertains to methods for preparing pharmaceutical formulations. In one embodiment, the method comprises:
  providing a peptidic compound and a carrier macromolecule;
  combining the peptidic compound and the carrier macromolecule under conditions such that a water-insoluble complex of the peptidic compound and the carrier macromolecule forms; and
  preparing a pharmaceutical formulation comprising the water-insoluble complex. For example, a solution of the peptidic compound and a solution of the carrier macromolecule are combined until a water-insoluble complex of the peptidic compound and the carrier macromolecule precipitates out of solution. In certain embodiments, the solutions of the peptidic compound and the carrier macromolecule are aqueous solutions. Alternatively, if the peptidic compound or the carrier molecule (or both) is not substantially water soluble prior to combination the two, then the peptidic compound and/or carrier macromolecule can be dissolved in a water-miscible solvent, such as an alcohol (e.g., ethanol) prior to combining the two components of the complex. In another embodiment of the method of preparing the water-insoluble complex, the solution of the peptidic compound and the solution of the carrier macromolecule are combined and heated until a water-insoluble complex of the peptidic compound and the carrier macromolecule precipitates out of solution. The amounts of peptidic compound and carrier macromolecule necessary to achieve the water-insoluble complex may vary depending upon the particular peptidic compound and carrier macromolecule used, the particular solvent(s) used and/or the procedure used to achieve the complex. Typically, however, the peptidic compound will be in excess relative to the carrier macromolecule on a molar basis. Often, the peptidic compound also will be in excess on a weight/weight basis, as demonstrated in the Examples. In certain embodiments, the carrier macromolecule, preferably carboxymethylcellulose sodium, and the peptidic compound, preferably PPI-149, are combined at a ratio of 0.2:1 (w/w) of carrier macromolecule:peptidic compound. In various other embodiments, the ratio of carrier macromolecule to peptidic compound (w/w) can be, for example, 0.5:1, 0.4:1, 0.3:1, 0.25:1, 0.15:1 or 0.1:1. Non-limiting examples of conditions and procedures for preparing a water-insoluble complex of the invention are described further in Example 1–5 and 8–9.

Once the peptidic compound/macromolecule complex precipitates out of solution, the precipitate can be removed from the solution by means known in the art, such as filtration (e.g., through a 0.45 micron nylon membrane), centrifugation and the like. The recovered paste then can be dried (e.g., in vacuo or in a 70° C. oven) and the solid can be milled or pulverized to a powder by means known in the art (e.g., hammer or gore milling, or grinding in mortar and pestle). Following milling or pulverizing, the powder can be sieved through a screen (preferably a 90 micron screen) to obtain a uniform distribution of particles. Moreover, the recovered paste can be frozen and lyophilized to dryness. The powder form of the complex can be dispersed in a carrier solution to form a liquid suspension or semi-solid dispersion suitable for injection. Accordingly, in various embodiments, a pharmaceutical formulation of the invention is a dry solid, a liquid suspension or a semi-solid dispersion. Examples of liquid carriers suitable for use in liquid suspensions include saline solutions, glycerin solutions and lecithin solutions.

In another embodiment, the pharmaceutical formulation of the invention is sterile formulation. For example, following formation of the water-insoluble complex, the complex can be sterilized, optimally by gamma irradiation or electron beam sterilization. Accordingly, the method of the invention for preparing a pharmaceutical formulation described above can further comprise sterilizing the water-insoluble complex by gamma irradiation or electron beam irradiation. Preferably, the formulation is sterilized by gamma irradiation using a gamma irradiation dose of at least 15 KGy. In other embodiments, the formulation is sterilized by gamma irradiation using a gamma irradiation dose of at least 19 KGy or at least 24 KGy. As demonstrated in Example 11, the formulations of the invention remain acceptably stable upon gamma irradiation.

Alternatively, to prepare a sterile pharmaceutical formulation, the water-insoluble complex can be isolated using conventional sterile techniques (e.g., using sterile starting materials and carrying out the production process aseptically). Accordingly, in another embodiment of the method for preparing a pharmaceutical formulation described above, the water-insoluble complex is formed using aseptic procedures.

Methods of forming a water-insoluble complex of the invention are described further in Examples 1–5 and 8–9. Pharmaceutical formulations, including powders, liquid suspensions, semi-solid dispersions, dry solids (e.g., lyophilized solids), and sterilized forms thereof (e.g., by gamma irradiation), prepared according to the methods of the invention, are also encompassed by the invention.

Yet another aspect of the invention pertains to methods of using the pharmaceutical formulations of the invention to treat a subject suffering from a condition treatable by the pharmaceutically active peptidic compound included in the water-insoluble complex. Accordingly, in a preferred embodiment, the invention provides a method for treating a subject for a condition treatable with an LHRH analogue, comprising administering to the subject a pharmaceutical formulation comprising a water-insoluble complex of an LHRH analogue and a carrier macromolecule.

The pharmaceutical formulation can be administered to the subject by any route suitable for achieving the desired therapeutic result(s), although preferred routes of administration are parenteral routes, in particular intramuscular (i.m.) injection and subcutaneous/intradermal (s.c./i.d.) injection. Alternatively, the formulation can be administered to the subject orally. Other suitable parental routes include intravenous injection, buccal administration, transdermal delivery and administration by the rectal, vaginal, intranasal or respiratory tract route. It should be noted that when a formulation that provides sustained delivery for weeks to months by the i.m or s.c./i.d. route is administered by an alternative route, there may not be sustained delivery of the agent for an equivalent length of time due to clearance of the agent by other physiological mechanisms (i.e., the dosage form may be cleared from the site of delivery such that prolonged therapeutic effects are not observed for time periods as long as those observed with i.m or s.c./i.d. injection).

The pharmaceutical formulation contains a therapeutically effective amount of the LHRH analogue. A "therapeutically effective amount" refers to an amount effective, at dosages and for periods of time necessary, to achieve the desired result. A therapeutically effective amount of an LHRH analogue may vary according to factors such as the disease state, age, and weight of the individual, and the ability of the LHRH analogue (alone or in combination with one or more other drugs) to elicit a desired response in the individual. Dosage regimens may be adjusted to provide the optimum therapeutic response. A therapeutically effective amount is also one in which any toxic or detrimental effects of the antagonist are outweighed by the therapeutically beneficial effects. A non-limiting range for a therapeutically effective amount of an LHRH analogue is 0.01 to 10 mg/kg. A preferred dosage of the LHRH analogue PPI-149 for sustained reduction of plasma testosterone levels for 28 days is approximately 0.1–10 mg/kg, more preferably 0.3–1.2 mg/kg (expressed as free peptide) in a liquid suspension volume of approximately 1 mL or less. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The treatment method of the invention can be applied to the treatment of various conditions, diseases and disorders in which administration of an LHRH analogue has a desired clinical effect. Examples of disease and disorders include hormone-dependent cancers, such as prostate cancer, breast cancer, ovarian cancer, uterine cancer and testicular cancer, benign prostatic hypertrophy, precocious puberty, endometriosis and uterine fibroids. Accordingly, the invention provides methods of treating these diseases and disorders by administering a pharmaceutical formulation of the invention. Additionally, LHRH analogues can be used to alter fertility. Accordingly, the methods of the invention also can be used in vitro fertilization and contraceptive purposes.

In a particularly preferred embodiment, the method is used to treat prostate cancer, the LHRH analogue used in the formulation is an LHRH antagonist, most preferably PPI-149, and the method allows for sustained delivery of the LHRH analogue in vivo for at least four weeks after administration by intramuscular or subcutaneous administration. An LHRH analogue, preferably PPI-149, formulated according to the invention can be used to inhibit growth of prostate cancer cells by administering the LHRH analogue to a subject suffering from prostate cancer. Moreover, an LHRH antagonist, preferably PPI-149, formulated according to the invention, can be used to inhibit the testosterone surge that accompanies the use of an LHRH agonist by preadministering the LHRH antagonist, preferably PPI-149, to a subject suffering from prostate cancer before initiating LHRH agonist therapy. Methods for inhibiting LHRH agonist-induced testosterone surge, and other methods for treating prostate cancer using LHRH antagonist, to which the formulations of the present invention can be applied, are described further in U.S. patent application Ser. No. 08/573,109, entitled "Methods for Treating Prostate Using LHRH Antagonists", filed Dec. 15, 1995, and a continuation-in-part patent application thereof, Ser. No. 08/755,593, also entitled "Methods for Treating Prostate Using LHRH Antagonists", filed Nov. 25, 1996, the contents of both of which are incorporated into published PCT application WO 97/22357. The entire contents of the U.S. applications and published PCT application are expressly incorporated herein by reference.

Specific processes for complexing a pharmaceutically active peptidic compound with a carrier macromolecule are set forth in Examples 1–5 and 8–9 below. Also described are test results that demonstrate that an LHRH antagonist-containing complex can enable sustained delivery of the pharmaceutically active peptide in vivo (Example 6) and can inhibit LHRH-agonist induced testosterone surge (Example 7). The following examples, which further illustrate the invention, should not be construed as limiting. The contents of all references, patents and published patent applications cited throughout this application are hereby incorporated by reference.

EXAMPLE 1

A 100 ml solution of the LHRH antagonist PPI-149 was prepared by dissolving 6.25 mg/ml of PPI-149 in water. An equal sample (100 ml minimum) of USP carboxymethylcellulose sodium (CMC) (low viscosity grade, Hercules Chemical Co.) was prepared at 0.125% w/v and mixed until dissolved. Equal portions of the PPI-149 and CMC solutions were mixed (giving a CMC:peptide ratio of 0.2:1 (w/w)) and a solid material was obtained. The solid material was stirred overnight and then collected by filtration over a 0.45 micron nylon filter. HPLC evaluation of the solution filtrate indicated at least 95% of the PPI-149 compound was converted to the solid complex. was removed from solution. The recovered white paste was rinsed twice with water and then transferred to a vial and dried in vacuo. Upon drying for 72 hours, 633 mg of a white powder was obtained. The solid material was then powdered in a mortar and pestle. Elemental analysis indicated 57% peptide in the complex.

EXAMPLE 2

25 mg of PPI-149 was dissolved in 1 ml of water. To this was added 1 ml of a 0.5% carboxymethylcellulose solution. The mixture formed a silky white solid upon mixing. The mixture was heated to reflux for five minutes and a flocculent white precipitate was formed. This material was isolated by centrifugation/decantation. The solid was resuspended in water and collected by repeated centrifugation. HPLC evaluation of the solution filtrate indicated at least 90% of the PPI-149 compound was converted to the solid complex. The white precipitate was dried in vacuo and the solid material was commuted in a mortar and pestle. Elemental analysis indicated 77% peptide in the complex.

EXAMPLE 3

50 mg of PPI-149 was dissolved in 2 mL of 5% mannitol and mixed with 2 mL of 0.5% carboxymethylcellulose (low viscosity, USP, Spectrum Quality Chemicals). The mixture was stirred and immediately yielded a white precipitate. The suspension was frozen and lyophilized to dryness to yield a PPI-149 sustained delivery complex.

EXAMPLE 4

25 mg of PPI-149 was dissolved in 1 mL water. To this was added 1 mL of 0.5% sodium alginate, USP (Spectrum). The mixture immediately formed a white precipitate upon mixing. This material was isolated by centrifugation/decantation. The solid was resuspended in water and collected by repeated centrifugation. The white precipitate was dried in vacuo. Elemental analysis was performed to obtain a peptide content of 66%.

EXAMPLE 5

25 mg of PPI-149 was dissolved in 1 mL water. Ammonia was added to adjust the pH to 11.0. To this was added 1 mL of 0.5% alginic acid, USP (Spectrum). The mixture immediately formed a white precipitate upon mixing. This material was isolated by centrifugation/decantation. The solid was resuspended in water and collected by repeated centrifugation. The white precipitate was dried in vacuo. Elemental analysis was performed to obtain a peptide content of 79%.

EXAMPLE 6

Figure 1B:
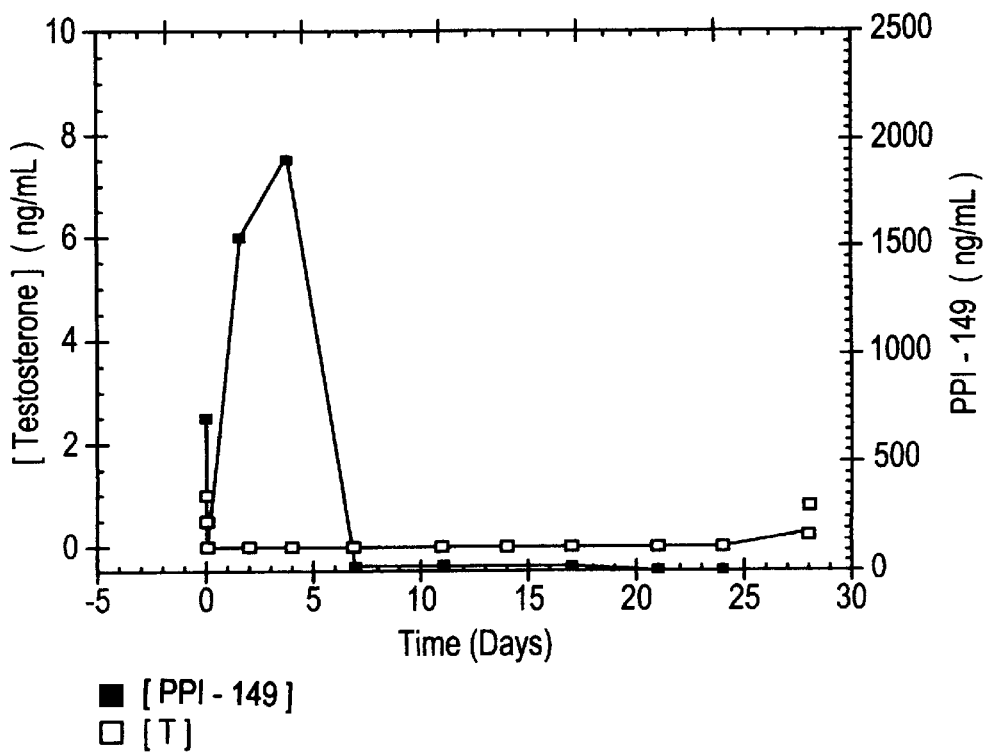

A water-insoluble complex of the LHRH antagonist PPI-149 and carboxymethylcellulose was prepared according to the preceding examples. A suspension of the PPI-149/CMC complex was prepared and a single dose was injected intramuscularly into rats and dogs. The dosage for the rats was 50 μg/kg/day×60 days and the dosage for the dogs was 40 μg/kg/day×28 days. Plasma testosterone levels (in ng/ml) were determined at various time points as a measure of the activity of the LHRH antagonist in the animal. Representative results, shown in the graph of FIG. 1, demonstrate that intramuscular injection of the PPI-149/CMC complex leads to sustained suppression of plasma testosterone levels for at least 42 days in the rats and at least 28 days in the dogs (indicated by the open boxes in FIG. 1), demonstrating sustained delivery of the LHRH antagonist. Plasma levels of PPI-149 (in ng/ml) were also monitored in the animals (indicated by the closed boxes in FIG. 1). An initial spike of PPI-149 was observed for about the first eight days, after which time PPI-149 was essentially undetectable in the plasma. Despite the inability to detect PPI-149 in the plasma beyond about day 8, the testosterone level results demonstrate that PPI-149 was still therapeutically active in vivo over the course of the experiment.

EXAMPLE 7

Figure 2:
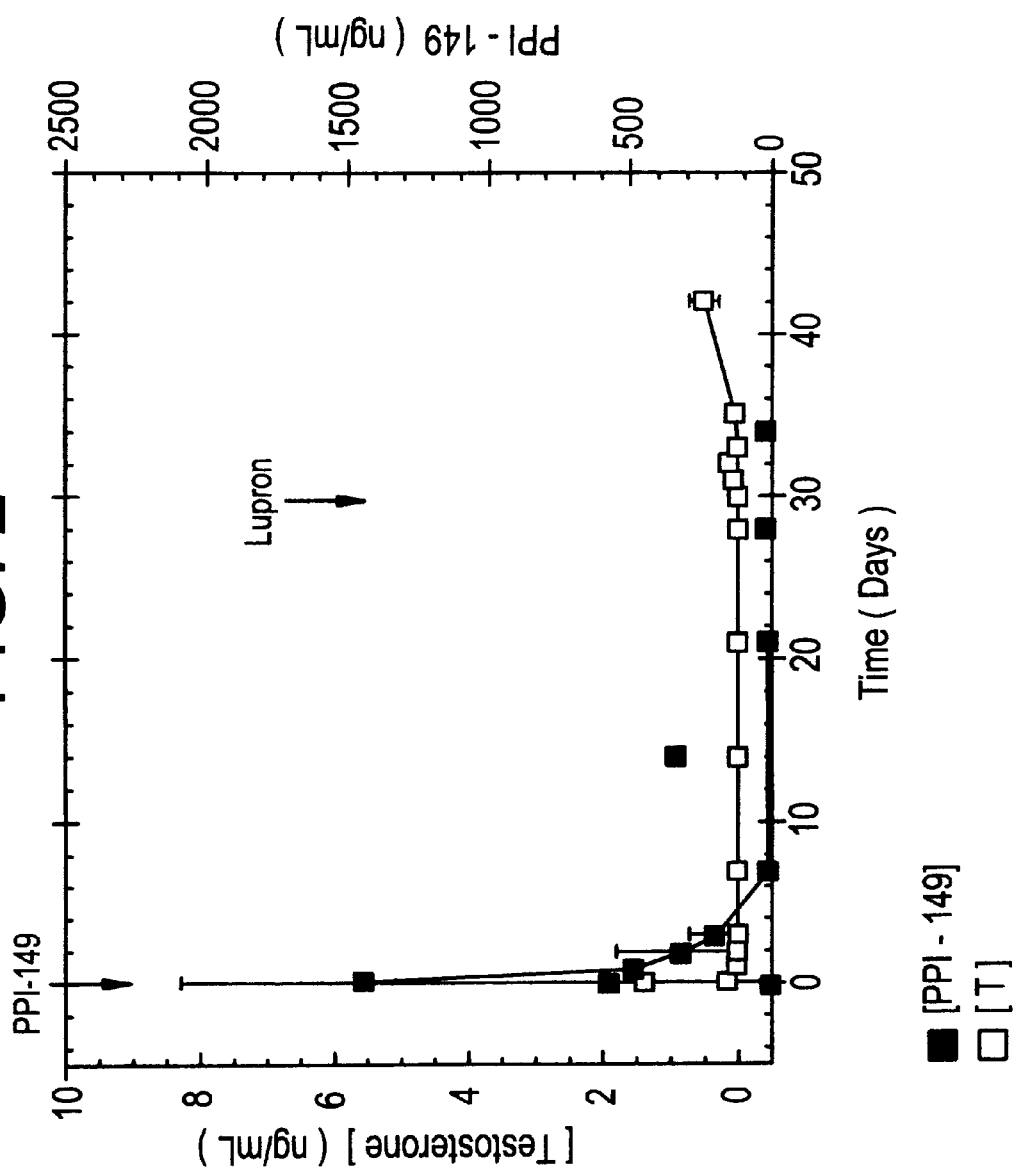
FIG. 2 is a graph depicting the plasma testosterone levels (in ng/ml; open boxes) and plasma PPI-149 levels (in ng/ml; closed boxes) in rats over time following intramuscular injection of a complex of the LHRH antagonist PPI-149 and carboxymethylcellulose on day 0 and injection of the LHRH agonist Lupron™ at day 30, demonstrating suppression of the Lupron™-induced testosterone surge by the PPI-149 pretreatment.

A water-insoluble complex of the LHRH antagonist PPI-149 and carboxymethylcellulose was prepared according to the preceding examples. A suspension of the PPI-149/CMC complex was prepared and a single dose was injected intramuscularly into rats on day 0. On day 30, the LHRH agonist Lupronrm (leuprolide) was injected into the rats. Plasma testosterone levels (in ng/ml; indicated by the open boxes in FIG. 2) were determined at various time points as a measure of the activity of the LHRH antagonist in the animal. Plasma levels of PPI-149 (in ng/ml) were also monitored in the animals (indicated by the closed boxes in FIG. 2). Representative results, shown in the graph of FIG. 2, demonstrate that pretreatment with the PPI-149/CMC complex rapidly reduces plasma testosterone to castration levels and, moreover, blocks the LHRH agonist-induced testosterone surge. Despite the inability to detect PPI-149 in the plasma beyond about day 8, the testosterone level results demonstrate that PPI-149 was still therapeutically active in vivo over the course of the experiment.

EXAMPLE 8

In this example, an insoluble complex was formed between the LHRH analogue PPI-258 and carboxymethylcellulose (CMC). PPI-258 has the structure: acetyl-D-napthylalanyl-D-4-Cl-phenylalanyl-D-pyridylalanyl-L-seryl-L-tyrosyl-D-asparaginyl-L-leucyl-L-Ne-isopropyl-lysyl-L-propyl-D-alanyl-amide. To prepare a PPI-258/CMC depot, 174.8 mg (148.6 mg net) of PPI-258 was added to 29.72 mL of water and the material was stirred to suspend and dissolve the peptide. To this stirred solution was added 1.85 mL of a 2% sodium CMC solution (Hercules). A solid precipitate was immediately observed. Upon heating to reflux, the suspension became translucent and then appeared as white precipitate. After a 5 minute reflux, the reaction was cooled and the solid was isolated by centrifugation. The solid was rinsed with water, and dried in vacuo overnight. The dried power was powdered in a mortar and pestle and sieved through a 90 micron stainless steel screen. The sieved powder (90 micron sieve) was collected and characterized. Total yields were 198.4 mg of dried solid which yielded 110.8 mg of sized powder after the milling step. Characterization provided the following compositional makeup of the complex: Peptide PPI-258—80%, CMC—18.8%, water—6.6%.

EXAMPLE 9

In this example, an insoluble complex was formed between the LHRH analogue Cetrorelix (also known as SB-75) and carboxymethylcellulose (CMC). Cetrorelix has the structure: acetyl-D-napthylalanyl-D-4-Cl-phenylalanyl-D-pyridylalanyl-L-seryl-L-tyrosyl-D-citrulyl-L-leucyl-L-arginyl-L-prolyl-D-alanyl-amide. To prepare a Cetrorelix/CMC depot, 102.8 mg (87 mg net) of Cetrorelix was added to 17.4 mL of water and the material was stirred to suspend and dissolve the peptide. To this stirred solution was added 1.1 mL of a 2% sodium CMC solution (Hercules). A clumpy white precipitate was immediately observed. The suspension was heated to reflux for 5 minutes and cooled to yield a solid white precipitate. The solid was isolated by centrifugation, was rinsed with water, and dried in vacuo overnight. The dried powder was powdered in a mortar and pestle and sieved through a 90 micron stainless steel screen. The powder was collected and characterized. Total yields were 95 mg of dried solid which yielded 60 mg of sized powder after the milling step. Characterization provided the following compositional makeup of the complex: Peptide Cetrorelix—75%, CMC—20.7%, water—6.5%

EXAMPLE 10

In this example, the sustained release of three different LHRH analogues, PPI-149, PPI-258 and Cetrorelix, prepared as CMC depot formulations as described in three previous examples, was examined in vivo. Three different formulation vehicles were tested, saline, glycerin (15% glycerin/4% dextrose) and lecithin. Sprague-Dawley rats (25 males, weight range 300–325 g) were used and the efficacy of the LHRH analogue was determined based on reduction in plasma testosterone levels.

The dosages and routes of administration were as follows:

| Group | Compound | Dose (mg/kg) | Dose ($\mu$g/kg/day) | Dose (mg/rat) | Vehicle | Route Admin. |
|---|---|---|---|---|---|---|
| A | PPI-149 | 9 | 300 | 2.7 | saline | IM |
| B | PPI-149 | 9 | 300 | 2.7 | glycerin | IM |
| C | PPI-149 | 9 | 300 | 2.7 | glycerin | SC |
| D | PPI-149 | 9 | 300 | 2.7 | lecithin | IM |
| E | PPI-258 | 9 | 300 | 2.7 | saline | IM |
| F | Cetrorelix | 9 | 300 | 2.7 | saline | IM |

The actual dose of peptide was 300 $\mu$g/kg/day for 30 days, which was 2.7 mg/rat given as a single 200 $\mu$L intramuscular (IM) or subcutaneous (SC) injection. The total volume required to inject 5 rats/group was 1.3 mL at a concentration of 13.5 mg/mL active peptide. The volume of injection was kept constant and the weight of the powder was adjusted for total peptide content, as follows:

| Group | Vol. Req. mL | Weight Req. mg Powder | Weight used mg Powder | Vol. used mL |
|---|---|---|---|---|
| A | 1.3 | 22.5 | 29.5 | 1.7 mL saline |
| B, C | 2.6 | 45 | 71.1 | 4.1 mL glycerin/dextrose |
| D | 1.3 | 22.5 | 35.2 | 2.03 mL 0.5% lecithin/mannitol |
| E | 1.3 | 22.5 | 31 | 1.79 mL saline |
| F | 1.3 | 22.5 | 20.9 | 1.21 mL saline |

A single 200 $\mu$L intramuscular, or subcutaneous injection of test article was made into the upper flank of the left hind limb or under the skin between the scapulae, respectively, on Day 0 under anesthesia.

To test plasma testosterone levels, approximately 0.4 mL of blood was removed from the retro-orbital sinus on Day 1 after dosing and at days 3, 7, 14, 21, 28 and 35. Blood was processed to plasma and frozen on dry ice for determination of testosterone plasma levels by standard methods.

Figure 3A:
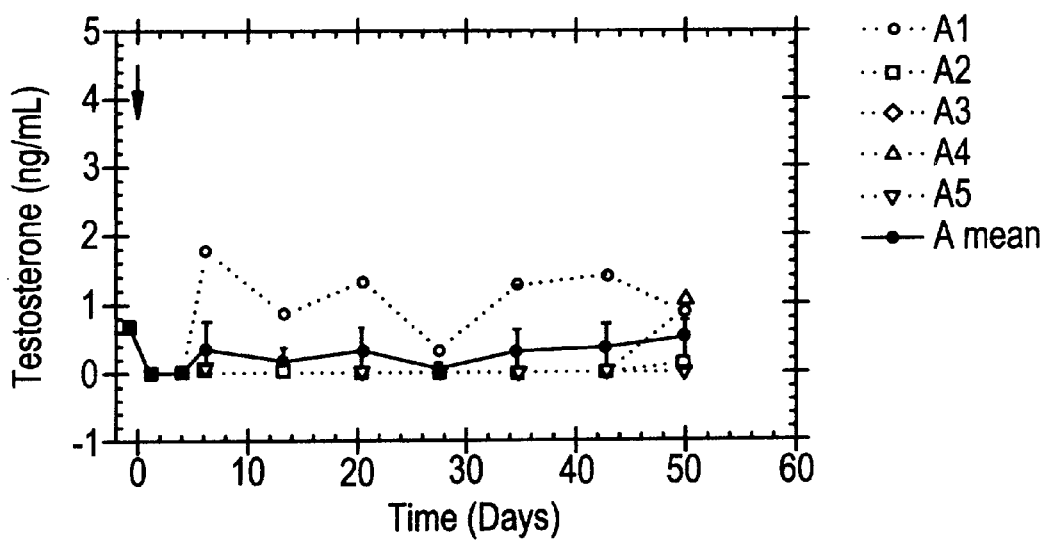
FIGS. 3A–3C are a series of graphs depicting the plasma testosterone levels (in ng/ml) in male Sprague-Dawley rats over time, following intramuscular injection of a PPI-149-CMC (FIG. 3A), PPI-258-CMC (FIG. 3B) or Cetrorelix™-CMC (FIG. 3C).
Figure 3B:
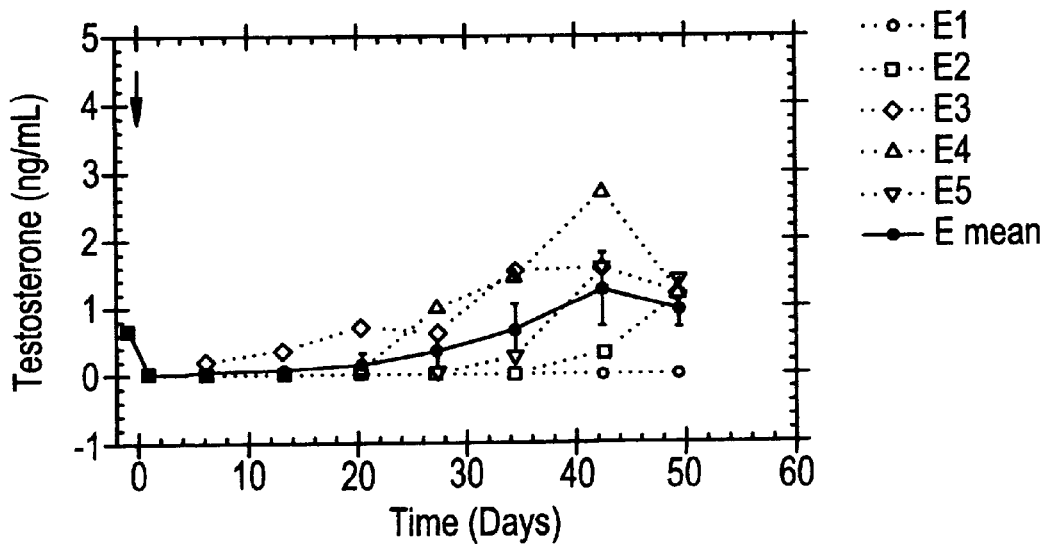
Figure 3C:
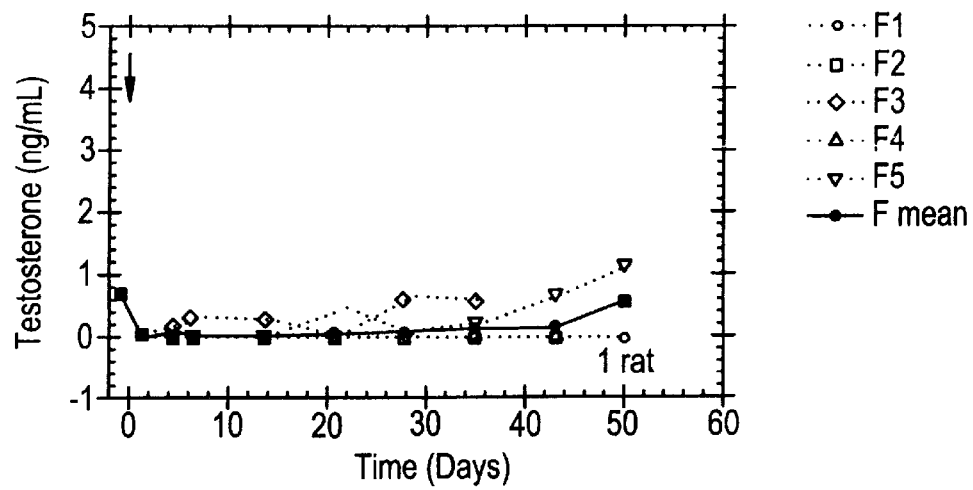

Representative results, shown in FIGS. 3A–3C, demonstrate that plasma testosterone levels in male Sprague-Dawley rats were reduced and maintained at low levels for at least 28 days and as long as 50 days in response to sustained release of the LHRH analogues PPI-149, PPI-258 and Centrolix prepared as CMC depot formulations (shown in FIGS. 3A, 3B and 3C, respectively). These results indicate that all three formulations are effective in reducing plasma testosterone levels in vivo and maintaining reduced plasma testosterone levels over time.

EXAMPLE 11

In this example, PPI-149-CMC formulations were exposed to gamma irradiation for purposes of sterilization, followed by evaluation of both physical and chemical properties of the irradiated formulations. Data described below indicate that γ-irradiation is a viable means of sterilization of PPI-149-CMC depot.

Peptide Stability

Approximately 40 mg of each of two separate PPI-149-CMC lots was packed separately (under an air headspace) in to a number of Type 1 Glass vials, sealed with rubber stoppers and aluminum seals. Vials were then subjected to a variety of nominal doses of gamma-irradiation. Two vials were analyzed for peptide purity (expressed as %) at each level of γ-irradiation exposure for each of the two lots. The results indicated that at γ-irradiation doses up to and including 24 KGy, PPI-149-CMC consistently exhibited less than a 2% reduction in peptide purity (as determined by HPLC impurity profile). A second study utilizing higher doses of gamma exposure was performed on an additional laboratory lot of PPI-149-CMC. PPI-149-CMC demonstrated remarkably good chemical stability when exposed to high γ-irradiation doses.

A subsequent preformulation study was implemented to compare the degradation profile obtained following PPI-149-CMC γ-irradiation with that obtained following autoclaving of PPI-149 injectable solution (1 mg/mL). Two samples were prepared: a) PPI-149-CMC exposed to 19 KGy γ-irradiation; b) A PPI-149 Solution (1 mg/mL) subjected to autoclaving (121° C./20 minutes). The HPLC chromatograms of the two samples demonstrated that the degradation profile for the two samples appeared to be qualitatively similar (given similar relative retention times of the major peaks).

Stressed Stability Storage Following Gamma-Irradiation

Stress-storage preformulation studies were also performed on vials post- gamma-irradiation. Sealed vials from two laboratory lots of PPI-149-CMC were exposed to 19 KGy gamma-irradiation and stored at 250° C., 37° C. and 50° C. for up to one month. The chemical stability data in these preformulation studies indicated that γ-irradiation at a dose of 19 KGy followed by stressed-storage stability did not result in major chemical instability even under highly stressed-storage conditions (e.g., 1 week at 50° C.). The data indicate at γ-irradiation doses up to and including 19 KGy, storage of PPI-149-CMC for up to 28 days at or below 50° C., consistently exhibited less than a 2% reduction in peptide purity (as determined by HPLC impurity profile). Despite an apparent difference in initial moisture content between the two lots studied, no significant difference in peptide purity was determined in either initial preformulation stability samples or those stored for up to a month.

PPI-149-CMC Particle Size Analysis

A particle size method using laser light scattering was developed, that is applicable to sizing studies of PPI-149-CMC. To illustrate the utility of the method, a preformulation experiment is presented, which was performed to investigate the effect of gamma-irradiation on the particle size of PPI-149-CMC. This experiment was conceived with the prior understanding that amorphous solid materials may be predisposed to particle consolidation, upon storage. Two samples of a laboratory lot of PPI-149-CMC were packed in type I glass vials, closed with gray butyl rubber stoppers and sealed with aluminum seals. Particle evaluation was performed prior to and following exposure to a gamma irradiation dose of 15.5 KGy. Particle evaluation was performed by laser light scattering (utilizing a Malvern Mastersizer S™ equipped with a reverse fourier lens). 20 mg samples for particle size analysis by laser light scattering were dispersed in approximately 0.5 mL deionised water by vigorous shaking, then sonicated in a bath at ambient temperature for 5 minutes. After running a background count, a method qualification experiment was performed. Sample dispersion was added drop-wise to the continuous feed reservoir (approximately 60 mL nominal volume) until approximately 20% obscuration was obtained. The mixer rotation speed was held at 2700 rpm throughout the experiment (plus background check). At this speed no vortex-induced bubbles were generated, but an adequately stable dispersion was maintained. Eight scans were performed, analysis of acquired data indicated a standard deviation of <0.03% as the extreme of any data point taken. When the sample dispersion was held in the reservoir for 15 minutes and then re-run, no significant change resulted, indicating the absence of particle dissolution over the course of the experiment.

Samples were analyzed using the experimental parameters given above. Eight scans were performed and mean particle diameter data was determined. Two distinct size distributions were noted, and all had a clean cut-off at the high-end particle size, indicating the absence of particle aggregation. One lot of PPI-149-CMC had apparently lower mean volume diameter prior to gamma irradiation than the sample post-irradiation. This preformulation study would seem to indicate some particle consolidation occurred during the sterilization process.

EXAMPLE 12

In this example, various preformulation experiments were performed to investigate the effect of both gamma-irradiation and temperature/humidity stress on the solid state form of PPI-149-CMC.

X-Ray Powder Diffraction

In the initial experiment, two 60 mg samples of PPI-149-CMC were packed (under an air headspace) in type I glass vials, closed with gray butyl rubber stoppers and sealed with aluminum seals. One sample was then exposed to a gamma-irradiation dose of 19.0 KGy. The solid state form of the two 60 mg Samples was then studied by X-ray powder diffraction. Diffractograms were compared prior to and following exposure to a gamma irradiation dose of 19.0 Kgy.

In a subsequent study, a 60 mg sample of PPI-149-CMC (post gamma-irradiation) was placed in a type I glass vial and placed in a pre-equilibrated constant humidity incubator at 50° C./75% Relative Humidity for 5 days. Immediately after withdrawal from the incubator, the sample container was closed with a gray butyl rubber stopper and sealed with an aluminum seal. The X-ray powder diffractogram of this stressed sample was then compared to another sample of the same lot that had been held at room temperature in a closed container. The samples were analyzed using a Siemens D500 automated Powder Diffractometer equipped with a graphite monochromator and a Cu ($\lambda$=1.54 Å) X-Ray source operated at 50 kV, 40mA. The two-theta scan range was 4–40° using a step scan window of 0.05°/1.2 second step. Beam slits were set at No. (1) 1°, (2) 1°, (3) 1°, (4) 0.15° and (5) 0.15° widths. Two-theta calibration was performed using an NBS mica standard (SRM 675). The samples were analyzed using a zero background sample plate.

The data indicated that prior to gamma irradiation, PPI-149-CMC had no apparent crystalline or pseudo-crystalline structure. In fact, it gave an X-ray powder diffraction pattern characteristic of an amorphous solid (a broad hump between 2–20° 2θ, with no significant peaks in the diffractogram). The PPI-149-CMC sample post-irradiation generated a very similar diffraction pattern to the non-irradiated sample, indicating that gamma-irradiation processing (at doses up to and including 19 KGy) does not apparently induce a solid-state polymorphic transition within the material. In a similar manner, the temperature/humidity stressed sample of PPI-149-CMC generated a very similar diffraction pattern to both the non-irradiated sample and the irradiated sample, which strongly suggests that PPI-149-CMC is not unduly prone to induction of solid-state polymorphic transitions within the material.

Hygroscopicity

Preformulation studies on PPI-149-CMC (post-irradiation) were performed to determine the equilibrium moisture uptake (measured by weight gain) at constant temperature (25° C.) under various conditions of relative humidity. Analysis of the equilibrium moisture (% water) as a function of relative humidity (% RH) indicated that moisture content gradually increased up to approximately 80% relative humidity. At high relative humidity (95% RH) PPI-149-CMC was capable of significant moisture sorption. At relative humidities at or below 80% RH, significant precautions in terms of protection from moisture are deemed unnecessary; thus certain manufacturing steps may be undertaken under ambient humidity conditions (provided humidity extremes are avoided).

EXAMPLE 13

In this example, dissolution studies on PPI-149-CMC were performed. Experiments were performed utilizing both sink and non-sink conditions. PPI-149-CMC has an approximate solubility of 100 μg/nL (measured and expressed as free peptide) at 250° C. in 0.1 M phosphate buffered saline at pH 7.3. Under sink conditions (defined as <10% of the saturated solubility in the system at a given temperature), even in the absence of stirring, PPI-149-CMC dissolved rapidly (measured and expressed as free peptide). In a similar experiment, the equilibrium solubility of PPI-149-CMC was determined (measured and expressed as free peptide) at 25° C. in 0.1M phosphate buffered saline at pH 7.3, using three samples: PPI-149-CMC alone, PPI-149-CMC in the presence of 10% additional (by weight) PPI-149 (expressed as free peptide, but introduced as PPI-149 with associated acetate) and PPI-149-CMC in the presence of 50% additional (by weight) Carboxymethylcellulose sodium USP. All three samples gave ostensibly a similar peptide equilibrium solubility. As the buffer system selected approximates physiological conditions, the presence of additional free Carboxymethylcellulose or peptide species present in PPI-149-CMC seems unlikely to affect solubility.

EXAMPLE 14

In this example, the pharmacokinetics, pharmacodynamics and safety of repeated subcutaneous (SC) and intramuscular (IM) doses of PPI-149-CMC were characterized in dogs.

In a first study, conducted for three months, forty male beagle dogs were evaluated, using monthly IM or SC injections of PPI-149-CMC at 1.2 mg/kg (Day 1), 0.3 or 0.6 mg/kg (Day 29) and 1.2 mg/kg (Day 57) in a variety of reconstitution vehicles. Eight groups of five dogs were assigned to the study as shown below:

| Group | N | Reconstitution Vehicle[a,b] Day 1 | Day 29 | Day 57 | Dose[c] (mg/kg) Day 1 | Day 29 | Day 57 | Route of Admin. |
|---|---|---|---|---|---|---|---|---|
| A[d] | 5 | Saline | Glycerin | Lecithin | 0 | 0 | 0 | IM |
| B | 5 | Glycerin | Glycerin | Lecithin | 1.2 | 0.3 | 1.2 | IM |
| C | 5 | Glycerin | Glycerin | Lecithin | 1.2 | 0.6 | 1.2 | IM |
| D | 5 | PEG | Glycerin | Lecithin | 1.2 | 0.3 | 1.2 | IM |
| E | 5 | PEG | Glycerin | Lecithin | 1.2 | 0.3 | 1.2 | SC |
| F[d] | 5 | Lecithin | Glycerin | Lecithin | 1.2 | 0.6 | 1.2 | IM |
| G[d] | 5 | Lecithin | Glycerin | Lecithin | 1.2 | 0.6 | 1.2 | SC |
| H | 5 | Glycerin | Glycerin | Lecithin | 1.2 | 0.3 | 1.2 | SC |

[a]Reconstitution vehicles are used to reconstitute PPI-149-CMC as a particular suspension.
They contain the following (in water):
1. Glycerin = 15% glycerin/5% dextrose
2. PEG = 4% polyethylene glycol-3350/4% mannitol
3. Lecithin = 0.5% lecithin/5% mannitol
[b]Note: the reconstitution vehicles to be used in clinical studies is 0.9% sodium chloride USP
[c]All doses are expressed in terms of peptide (PPI-149) content.
[d]Three animals were sacrificed at Day 85 for complete anatomical and microscopic histology.

This study was designed such that the efficacy of PPI-149-CMC at an initial dose in different vehicles was assessed during the first month of treatment. During the second month on-study, the dogs received lower doses of PPI-149-CMC in an attempt to determine an efficacious "maintenance" dose. The third month was scheduled to evaluate the long term safety and efficacy characteristics of PPI-149-CMC.

IM or SC doses of PPI-149-CMC formulated in one of the reconstitution vehicles, or IM doses of control article, were administered on each dosing day into the upper flank of the right hind limb (IM) or in the mid-scapular region (SC). Material was drawn into a 1cc tuberculin syringe with a 23 g short bevel needle. The injection site was wiped with an alcohol swab immediately prior to dosing. The volume injected was based on a specific dose of peptide/kg body weight. It should be noted that all doses refer to the amount of PPI-149 peptide administered.

Each animal was observed at least twice daily during the entire study for overt signs of toxic or pharmacologic effect and changes in general behavior and appearance. All abnormal clinical observations were recorded.

Blood was collected prior to administration of the first dose and at various times following dosing, for complete blood counts (CBC), serum chemistry analysis, and determination of PPI-149 and testosterone concentrations twice weekly by radioimmunoassays.

After three months on-study, nine animals were sacrificed and their tissues collected for gross pathological and histo-pathological analysis. Animals were selected for sacrifice from the vehicle control group, one of the IM dosing groups and one of the SC dosing groups. The tissues collected for gross pathology and histopathology at the 3 month sacrifice were: administration Site (SC or IM), adrenal glands, aorta, bone, bone marrow, brain, diaphragm, epididymis, esophagus, eyes with optic nerve, heart, kidneys, large intestine (cecum, colon), liver with gall bladder, lungs with bronchi, lymph nodes, pancreas, pituitary gland, prostate gland with urethra, salivary glands, sciatic nerve, skeletal muscle, skin, small intestine (duodenum, jejunum, ileum), spinal cord, spleen, stomach, testes, thymus, thryoid gland with parathyroid, tongue, trachea, urinary bladder and gross lesions.

There were no significant changes in hematology or blood chemistry from baseline during the study for either treated or control animals. Gross and histological evaluation at the three month sacrifice showed no apparent differences between PPI-149-CMC treated dogs and control (vehicle-treated) animals, with the exception of changes in the testes and prostate, as expected with this LHRH antagonist.

Regarding PPI-149-CMC pharmacokinetics, all dogs treated with 1.2 mg/kg PPI-149-CMC resuspended in a variety of reconstitution vehicles and administered IM or SC showed similar plasma PPI-149 pharmacokinetic profiles, with plasma concentration peaking within the first 2 days and then decreasing slowly in an exponential manner over the following month. PPI-149-CMC gave similar plasma distribution of PPI-149 when suspended in any of the three reconstitution vehicles used in the study.

Regarding PPI-149-CMC endocrine efficacy, castrate levels of testosterone (<0.6 ng/mL) were observed within 24 hours of initiation of PPI-149-CMC dosing in all dogs, and levels generally remained in the castrate range throughout the first month regardless of the route of administration or choice of reconstitution vehicle. Twenty-six (26) of 35 dogs (75%) had castrate levels of testosterone in a blood sample obtained immediately prior to administration of the second dose of PPI-149-CMC on Day 29. These results indicate that an initial dose of 1.2 mg/kg in dogs successfully induces a rapid, long-lasting suppression (>28 days) in plasma testosterone. In the second month of dosing, when the efficacy of a "maintenance" dose (a dose lower than the initial dose) was investigated, the results indicated that administration of 0.3 or 0.6 mg/kg of PPI-149-CMC maintained castrate levels of testosterone for more than 20 days in 30 out of 35 dogs. At the end of the second month of treatment (Day 57), 21 of 35 dogs (60%) remained castrate, while 14 animals had testosterone in the normal range (>0.6% ng/mL). A dose of 1.2 mg/kg was administered in the beginning of the third month. Plasma concentrations of PPI-149 were sustained for the following twenty-eight day period while plasma levels of testosterone were again "castrate." By the end of the third month (Day 85), plasma levels of testosterone were shown to be in the castrate range in 30 of 35 PPI-149-CMC-treated dogs.

In summary, thirty-five (35) dogs received 1.2 mg/kg PPI-149-CMC on Day 1, 0.3 or 0.6 mg/kg PPI-149-CMC on Day 29 and 1.2 mg/kg PPI-149-CMC on Day 57, using IM or SC dosing with a variety of reconstitution vehicles. Of these 35 dogs, 19 animals (54%) had plasma testosterone levels which remained in the castrate range throughout the entire course of therapy. Thus, administration of PPI-149-CMC at 28 day intervals was able to result in complete suppression of plasma testosterone which is rapid (all animals had castrate levels within 24 hours) and long-lasting (maintained throughout the course of administration).

Figure 4:
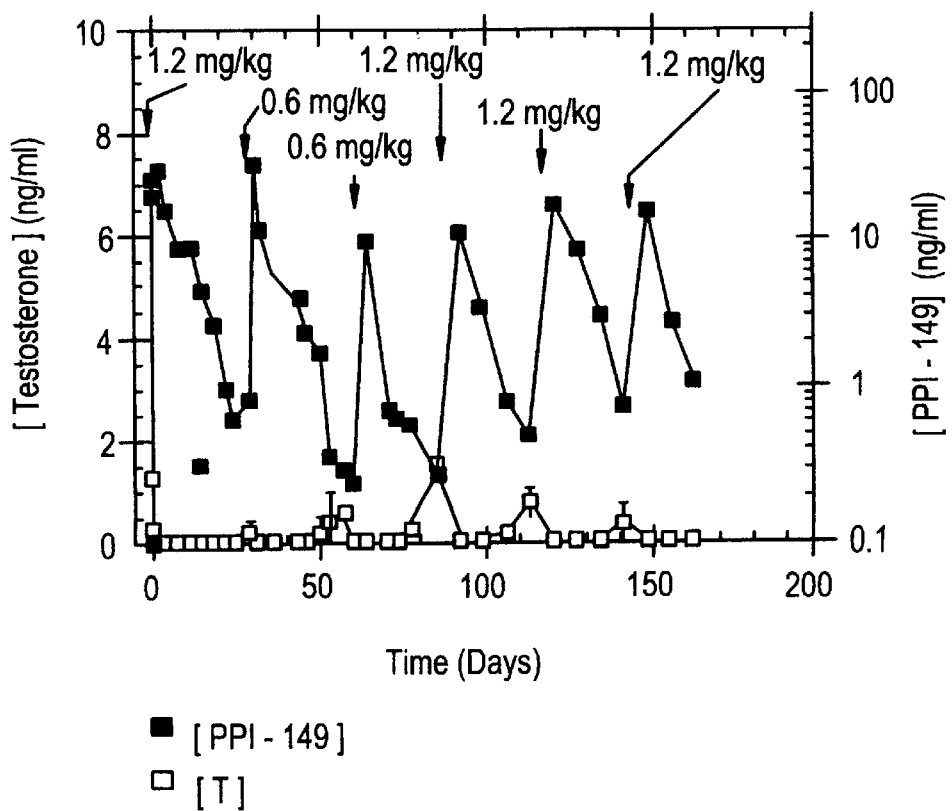
FIG. 4 is a graph depicting the plasma testosterone levels (in ng/ml; open boxes) and plasma PPI-149 levels (in ng/ml; closed boxes) in dogs over time following subcutaneous injection of PPI-149-CMC at the indicated dosages at 28 day intervals, demonstrating prolonged suppression of plasma testosterone levels.
Figure 5:
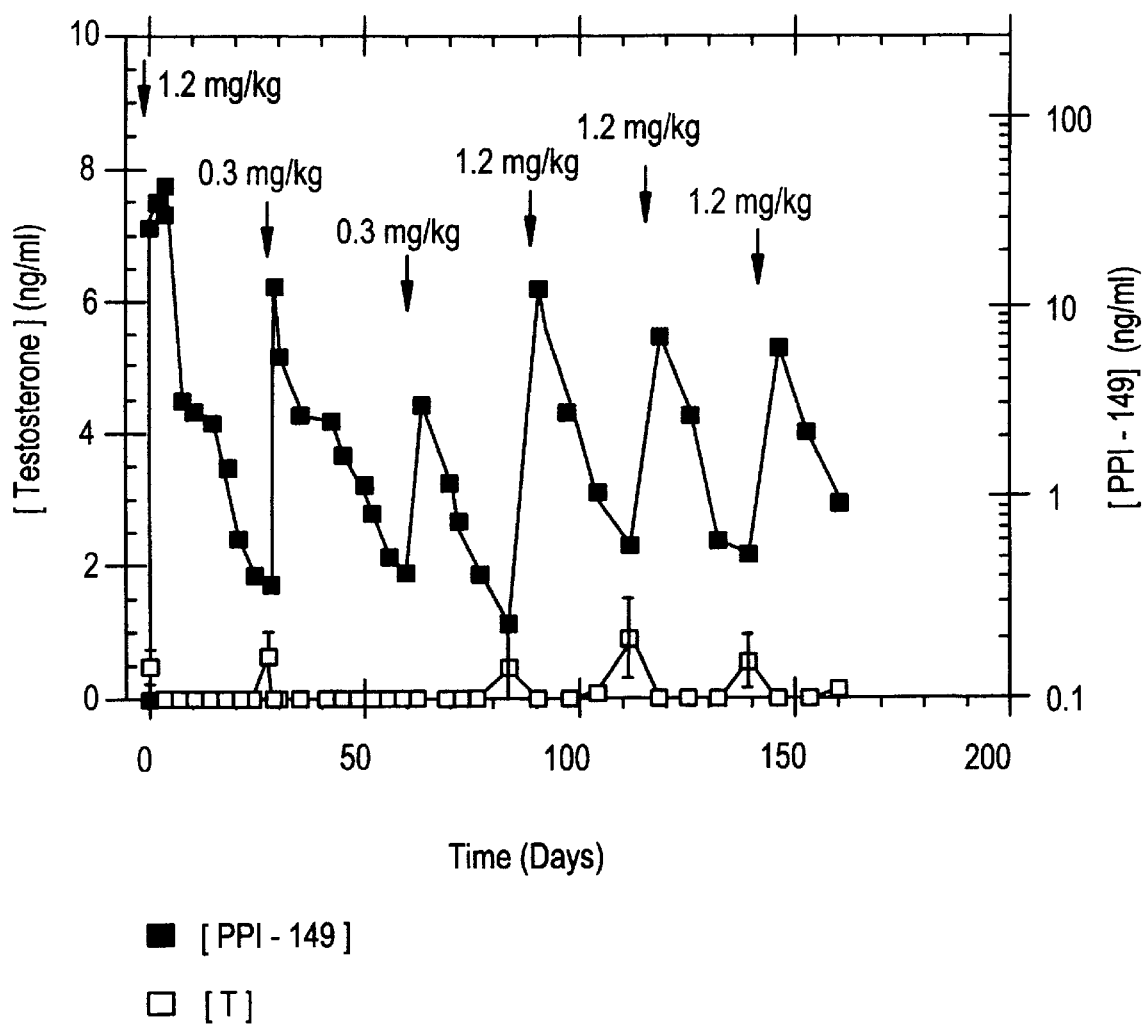
FIG. 5 is a graph depicting the plasma testosterone levels (in ng/ml; open boxes) and plasma PPI-149 levels (in ng/ml; closed boxes) in dogs over time following intramuscular injection of PPI-149-CMC at the indicated dosages at 28 day intervals, demonstrating prolonged suppression of plasma testosterone levels.

A similar study to that described above was conducted for six months in dogs to further evaluate the long term safety and efficacy characteristics of PPI-149-CMC. Animals received an initial dose of 1.2 mg/kg PPI-149-CMC either IM or SC and five subsequent doses (at a concentration of either 0.3 mg/kg, 0.6 mg/kg or 1.2 mg/kg) at 28 day intervals. Plasma testosterone and PPI-149 levels were evaluated by radioimmunoassay at regular intervals. Representative results are shown in FIG. 4 (for SC treatment) and FIG. 5 (for IM treatment), which illustrate plasma testosterone levels (open boxes) and PPI-149 levels (closed boxes). The particular dosages used at each administration of PPI-149-CMC are shown on the graphs. The results illustrated in FIGS. 4 and 5 further demonstrate that administration of PPI-149-CMC at 28 day intervals was able to result in complete suppression of plasma testosterone which is rapid and long-lasting, with reduced plasma testosterone levels being maintained for as long as six months.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A packaged formulation for treating a subject for a condition treatable with an LHRH analogue, comprising:
a solid ionic complex of an LHRH angalogue and a carrier macromolecule packaged with instructions for fusing the complex for treating a subject having a condition treatable with an LHRH analogue, wherein the peptide content of said complex is 57% to 80% by weight.

2. The packaged formulation of claim 1, wherein the LHRH analogue has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH, and the carrier macromolecule is carboxymethylcellulose, or a pharmaceutically acceptable salt thereof.

3. In a syringe having a lumen, the improvement comprises, inclusion of a liquid suspension of a solid ionic complex of an LHRH analogue and a carrier macromolecule in the lumen, wherein the peptide content of said complex is 57% to 80% by weight.

4. The syringe of claim 3, wherein the LHRH analogue has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH, and the carrier macromolecule is carboxymethylcellulose, or a pharmaceutically acceptable salt thereof.

5. A method for treating a subject for a condition treatable with an LHRH analogue, comprising administering to the subject a pharmaceutical formulation comprising a solid ionic complex of an LHRH analogue and a carrier macromolecule, wherein the peptide content of said complex is 57% to 80% by weight.

6. The method of claim 5, wherein the complex provides sustained delivery of the LHRH analogue to a subject for at least one week after the pharmaceutical composition is administered to the subject.

7. The method of claim 5, wherein the complex provides sustained delivery of the LHRH analogue to a subject for at least two weeks after the pharmaceutical composition is administered to the subject.

8. The method of claim 5, wherein the complex provides sustained delivery of the LHRH analogue to a subject for at least three weeks after the pharmaceutical composition is administered to the subject.

9. The method of claim 5, wherein the complex provides sustained delivery of the LHRH analogue to a subject for at least four weeks after the pharmaceutical composition is administered to the subject.

10. The method of claim 5, wherein the LHRH analogue is an LHRH antagonist.

11. The method of claim 10, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

12. The method of claim 5, wherein the carrier macromolecule is an anionic polymer.

13. The method of claim 5, wherein the carrier macromolecule is an anionic polyalcohol derivative, or fragment thereof, or a pharmaceutically acceptable salt thereof.

14. The method of claim 5, wherein the carrier macromolecule is an anionic polysaccharide derivative, or fragment thereof, or a pharmaceutically acceptable salt thereof.

15. The method of claim 5, wherein the carrier macromolecule is carboxymethylcellulose, or a pharmaceutically acceptable salt thereof.

16. The method of claim 5, wherein the carrier macromolecule is selected from the group consisting of align, alginate, anionic acetate polymers, anionic acrylic polymers, xantham gums, anionic carageenan derivatives, anionic polygalacturonic acid derivatives, sodium starch glycolate, and fragments, derivatives and pharmaceutically acceptable salts thereof.

17. The method of claim 5, wherein the pharmaceutical formulation is administered to the subject by a parenteral route.

18. The method of claim 5, wherein the pharmaceutical formulation is administered to the subject orally.

19. The method of claim 5, wherein the pharmaceutical formulation is administered by intramuscular injection or subcutaneous/intradermal injection.

20. The method of claim 5, wherein the condition treatable with an LHRH analogue is a hormone dependent cancer.

21. The method of claim 20, wherein the hormone dependent cancer is prostate cancer.

22. The method of claim 5, wherein the condition treatable with an LHRH analogue is selected from the group consisting of benign prostatic hypertrophy, precocious puberty, endometriosis and uterine fibroids.

23. The method of claim 5, wherein the LHRH analogue is administered for in vitro fertilization or contraceptive purposes.

24. A pharmaceutical composition comprising a solid ionic complex of a pharmaceutically active peptide and a carrier macromolecule, wherein the peptide content of said complex is 57% to 80% by weight.

25. A pharmaceutical composition consisting essentially of a solid ionic complex of a pharmaceutically active peptide and a carrier macromolecule, wherein the peptide content of said complex is 57% to 80% by weight.

26. The pharmaceutical composition of any one of claim 24 or 25, wherein the pharmaceutically active peptide is cationic and the carrier macromolecule is anionic.

27. The pharmaceutical composition of any one of claim 24 or 25, wherein the pharmaceutically active peptidic compound is aniotic and the currier macromolecule is cationic.

28. The pharmaceutical composition of any one of claim 24 or 25, wherein the complex provides sustained delivery of the pharmaceutically active peptide to a subject for at least one week after the pharmaceutical composition is administered to the subject.

29. The pharmaceutical composition of any one of claim 24 or 25, wherein the complex provides sustained delivery of the pharmaceutically active peptide to a subject for at least two weeks after the pharmaceutical composition is administered to the subject.

30. The pharmaceutical composition of any one of claim 24 or 25, wherein the complex provides sustained delivery of the pharmaceutically active peptide to a subject for at least three weeks after the pharmaceutical composition is administered to the subject.

31. The pharmaceutical composition of any one of claim 24 or 25, wherein the complex provides sustained delivery of the pharmaceutically active peptide to a subject for at least four weeks after the pharmaceutical composition is administered to the subject.

32. The pharmaceutical composition of any one of claim 24 or 25, wherein the pharmaceutically active peptide is a multivalent cationic or anionic peptide.

33. The pharmaceutical composition of any one of claim 24 or 25, wherein the peptide is 5 to 20 amino acids in length.

34. The pharmaceutical composition of any one of claim 24 or 25, wherein the peptide is 1 to 15 amino acids in length.

35. The pharmaceutical composition of any one of claim 24 or 25, wherein the peptide is 8 to 12 amino acids in length.

36. The pharmaceutical composition of any one of claim 24 or 25, wherein the carrier macromolecule is an anionic polymer.

37. The pharmaceutical composition of any one of claim 24 or 25, wherein the carrier macromolecule is an anionic polyalcohol derivative, or fragment thereof.

38. The pharmaceutical composition of any one of claim 24 or 25, wherein the carrier macromolecule is an anionic polysaccharide derivative, or fragment thereof.

39. The pharmaceutical composition of any one of claim 24 or 25, wherein the carrier macromolecule is carboxymethylcellulose, or a fragment or derivative thereof.

40. The pharmaceutical composition of any one of claim 24 or 25, wherein the carrier macromolecule is selected from the group consisting of align, alginate, anionic acetate polymers, anonic acrylic polymers, xantham gums, anionic carageenan derivatives, anionic polygalacturonic acid derivatives, sodium starch glycolate, and fragments, derivatives and pharmaceutically acceptable salts thereof.

41. The pharmaceutical composition of any one of claim 24 or 25, which is a lyophilized solid.

42. The pharmaceutical composition of any one of claim 24 or 25, wherein said solid ionic complex is suspended as a liquid suspension or dispersed as a semi-solid dispersion.

43. The pharmaceutical composition of any one of claim 24 or 25, wherein said pharmaceutically active peptide is an LHRH analogue.

44. The pharmaceutical composition of claim 43 wherein the LHRH analogue is an LHRH antagonist comprising a peptide compound, wherein a residue of the peptide compound corresponding to the amino acid at position 6 of natural mammalian LHRH comprises a D-asparagine structure.

45. The pharmaceutical composition of claim 43 wherein the LHRH analogue is an LHRH antagonist comprising a peptide compound comprising a structure: A-B-C-D-E-F-G-H-I-J
wherein
 A is pyro-Glu, Ac-D-Nal , Ac-D-Qal, Ac-Sar, or Ac-D-Pal
 B is His or 4-Cl-D-Phe
 C is Trp, D-Pal, D-Nal, L-Nal, D-Pal(N-O), or D-Trp
 D is Ser
 E is N-Me-Ala, Tyr, N-Me-Tyr, Ser, Lys(iPr), 4-Cl-Phe, His, Asn, Met, Ala, Arg or Ile;
 F is D-Asn, D-Gln, or D-Thr;
 G is Leu or Trp;
 H is Lys(iPr), Gln, Met, or Arg
 I is Pro; and
 J is Gly-$NH_2$ or D-Ala-$NH_2$;
or a pharmaceutically acceptable salt thereof.

46. The pharmaceutical composition of claim 43, wherein the LHRH analogue is an LHRH antagonist having the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

47. The pharmaceutical composition of claim 43 wherein said pharmaceutically active peptide is an LHRH antagonist.

48. The pharmaceutical composition of claim 43, wherein the LHRH analogue is the LHRH agonist Leuprolide having the structure pGlu-His-Trp-Ser-Tyr-D-Leu-Leu-Arg-Pro (ethylamide)-Gly.

49. The pharmaceutical composition of claim 43, wherein the LHRH analogue is the LHRH antagonist Cetrorelix having the structure Ac-D-Nal-4-Cl-D-Phe-D-Pal-Ser-Tyr-D-Cit-Leu-Arg-Pro-D-Ala.

50. The pharmaceutical composition of any one of claim 24 or 25, wherein said pharmaceutically active peptide is selected from the group consisting of bradykinin analogues, parathyroid hormone, adenocorticotrophic hormone, calcitonin, and vasopressin analogues.

* * * * *